United States Patent [19]

Freytag

[11] 4,434,236

[45] Feb. 28, 1984

[54] IMMUNOASSAY WHEREIN LABELED ANTIBODY IS DISPLACED FROM IMMOBILIZED ANALYTE-ANALOGUE

[75] Inventor: J. William Freytag, Wilmington, Del.

[73] Assignee: E. I. Du Pont de Nemours & Co., Wilmington, Del.

[21] Appl. No.: 435,454

[22] Filed: Oct. 20, 1982

[51] Int. Cl.$^3$ .................... G01N 33/54; G01N 33/56; G01N 33/58

[52] U.S. Cl. .................... 436/512; 210/656; 435/7; 436/527; 436/529; 436/530; 436/531; 436/532; 436/536; 436/541; 436/815

[58] Field of Search .............. 436/512, 531, 536, 541, 436/815, 527, 529, 532, 530; 435/7; 210/656

[56] References Cited

U.S. PATENT DOCUMENTS

| | | | |
|---|---|---|---|
| 4,039,652 | 8/1977 | Adams | 436/541 X |
| 4,119,709 | 10/1978 | Holub | 436/541 X |
| 4,125,492 | 11/1978 | Cuatrecasas | 210/656 X |
| 4,185,084 | 1/1980 | Mochida | 436/541 X |
| 4,235,869 | 11/1980 | Schwarzberg | 435/7 X |
| 4,235,960 | 11/1980 | Sasse | 435/7 |
| 4,256,725 | 3/1981 | Rutner | 436/810 X |
| 4,257,884 | 3/1981 | Lim | 210/656 |
| 4,298,593 | 11/1981 | Ling | 435/7 X |
| 4,330,299 | 5/1982 | Cerami | 436/169 X |

OTHER PUBLICATIONS

Chemical Abstracts, 89:2805c (1978).

*Primary Examiner*—Sidney Marantz

[57] ABSTRACT

A method for the rapid determination of analyte in a sample is provided. The sample is contacted with a solid phase having immobilized thereon an analyte-analogue to which there is displaceably bound a labeled anti-analyte antibody. Because the antibody has greater affinity for the analyte than the analyte-analogue, the labeled antibody is displaced from the solid phase. The complex is separated from the solid phase, and the amount of complex is measured. The measured amount is related to the amount of analyte initially present in the sample.

10 Claims, 2 Drawing Figures

IMMUNOASSAY WHEREIN LABELED ANTIBODY IS DISPLACED FROM IMMOBILIZED ANALYTE-ANALOGUE

BACKGROUND OF THE INVENTION

1. Field of the Invention

This invention relates to heterogeneous immunoassays for analytes having antigenic or haptenic properties, and more specifically to a heterogeneous immunoassay in which an analyte in a sample preferentially binds to and displaces labeled antibody bound to an analyte-analogue immobilized on a solid phase.

2. Description of Background Art

A large and expanding market exists for clinical laboratory diagnostic tests which can be used for the rapid and accurate determination of the concentrations of various organic analytes present in biological fluids, frequently present at micromolar concentrations or less.

In recent years, a number of immunoassay techniques have been developed for the measurement of such analytes. These immunoassays are based on the haptenic or antigenic property of the analytes, i.e., the ability to elicit specific anti-analyte antibody when injected into an animal host. A typical competitive binding immunoassay utilizes a labeled analyte, unlabeled analyte and an anti-analyte antibody, all of which participate in competitive binding reactions to produce two species of the labeled analyte, a bound-species and a free-species. The relative amounts of bound-species and free-species are a function of the analyte concentration in the test sample.

If the labeled analyte in the bound-species and that in the free-species are essentially indistinguishable by the means used to measure the label, the bound-species and free-species must be physically separated. The type of assay in which a separation step is required is referred to as a heterogeneous assay.

Two widely used heterogeneous immunoassays are the radioimmunoassay (RIA) and the enzyme-linked immunosorbent assay (ELISA). In the RIA, a sample containing an unknown amount of unlabeled analyte is mixed with a known amount of radiolabeled analyte and anti-analyte antibody. The system is allowed to react to near-equilibrium and then a separation step is employed to separate the antibody-bound analyte from the free analyte. Since unlabeled analyte and labeled analyte compete for a limited number of antibody binding sites, the more unlabeled analyte, the less labeled analyte will be detected in the bound fraction (or the more in the free fraction). This process is generally time-consuming (1–3 hours) and labor intensive.

Recently, the RIA has been automated by immobilizing the antibody on a porous support. After the sample containing unlabeled analyte is mixed with a known amount of labeled analyte, the sample is percolated through a column containing a limited number of immobilized antibody binding sites. Either the free or bound label can be quantified. One disadvantage of this method is that it requires very precise column synthesis in order to insure accurate and reproducible measurements of analyte concentration.

ELISA is similar in principle to RIA except that the labeling substance is an enzyme such as $\beta$-galactosidase or alkaline phosphatase rather than a radioisotope.

In addition to enzymes and isotopes, numerous other labeling substances have been described in the literature. These include fluorophores (e.g., fluorescein, rhodamine), coenzymes (e.g., FAD), bio- and chemiluminescent materials (e.g., luciferin), enzyme inhibitors (e.g., phosphonates), etc.

The use of an affinity column to effect the separation step has been described in French Patent Appl. No. 79,15992, published Jan. 9, 1981. It discloses the use of a gel having coupled to it a ligand which has affinity for the labeling substance and which additionally has molecular sieving properties. The use of a gel having affinity for the ligand of interest rather than for the labeling substance and having molecular sieving properties is also contemplated.

U.S. Pat. No. 3,654,090, issued Apr. 4, 1972, to Schuurs et al., describes a noncompetitive heterogeneous immunoassay for human chorionic gonadotropin (HCG) which uses an excess of enzyme-labeled divalent antibody and a column having immobilized HCG to accomplish the separation step. This assay is limited in sensitivity by the fact that one cannot distinguish between an antibody with one molecule of HCG bound and an antibody with no HCG bound. Both species will be retained by the affinity column.

Girma et al., Brit. J. Haematol, Volume 47, 269 (1981), describe a two-site radioimmunometric assay (IRMA) for coagulation factor VIII in which monovalent Fab fragments of antibodies are used. Their results indicate that a ten-fold higher sensitivity can be attained using monovalent rather than divalent antibodies.

U.S. Pat. No. 4,298,593, issued Nov. 3, 1981 to Ling, discloses a method for immunochemically assaying a member of an antigen-antibody binding pair which utilizes labeled antigen having a plurality of antigenic binding sites immunochemically bound to labeled Fab as the indicating reagent. This assay suffers from the disadvantage that haptens (having only a single antigenic binding site) cannot be used.

U.S. Pat. No. 4,200,436, issued Apr. 29, 1980 to Mochida et al., discloses an immunochemical measuring process using a labeled, monovalent antibody and an insolubilized antigen. This assay suffers from the disadvantage that sample containing analyte must be pre-incubated with the anti-analyte/label conjugate. Pre-incubation steps are time-consuming and difficult to automate.

Cocola et al., Analyt. Biochem., Volume 99, 121 (1979), describe a release radioimmunoassay for the determination of human chorionic somatomammotropin wherein a radiolabeled antigen is released from a labeled antigen/antibody complex-coated cellulose disk in an amount proportional to the amount of antigen present in the test sample. This method suffers from the disadvantage that the affinity of the immobilized antibody for labeled and unlabeled antigen is the same. Thus, in order to get substantial release of the label, long incubation times (18 hours) or inclusion of a chaotropic agent (4M urea) are desirable.

There is a need for a heterogeneous immunoassay which does not require a pre-incubation step and which is readily adaptable to automated or semi-automated instrumentation.

SUMMARY OF THE INVENTION

The method of this invention comprises the following steps:

(1) contacting a liquid sample suspected of containing analyte with a solid phase having immobilized thereon an analyte-analogue to which there is displaceably bound a labeled, anti-analyte antibody in molar excess over the analyte, wherein the dissociation constant between said antibody and the analyte-analogue is greater than the dissociation constant between said antibody and the analyte, whereby said antibody is displaced from the immobilized analyte-analogue as said antibody forms a complex with the analyte from the liquid sample;

(2) separating said complex from the solid phase; and (3) measuring the amount of said complex which is related to the amount of analyte initially present in the liquid sample.

In a preferred embodiment, the anti-analyte antibody is monovalent, and the solid phase is a material such as beaded agarose or cross-linked dextran, packed in a column through which sample containing analyte is percolated. This assay is applicable to analytes having antigenic or haptenic properties, requires no pre-incubation of sample with labeled antibody, and is readily automated.

DETAILED DESCRIPTION OF THE INVENTION

Figure 1:
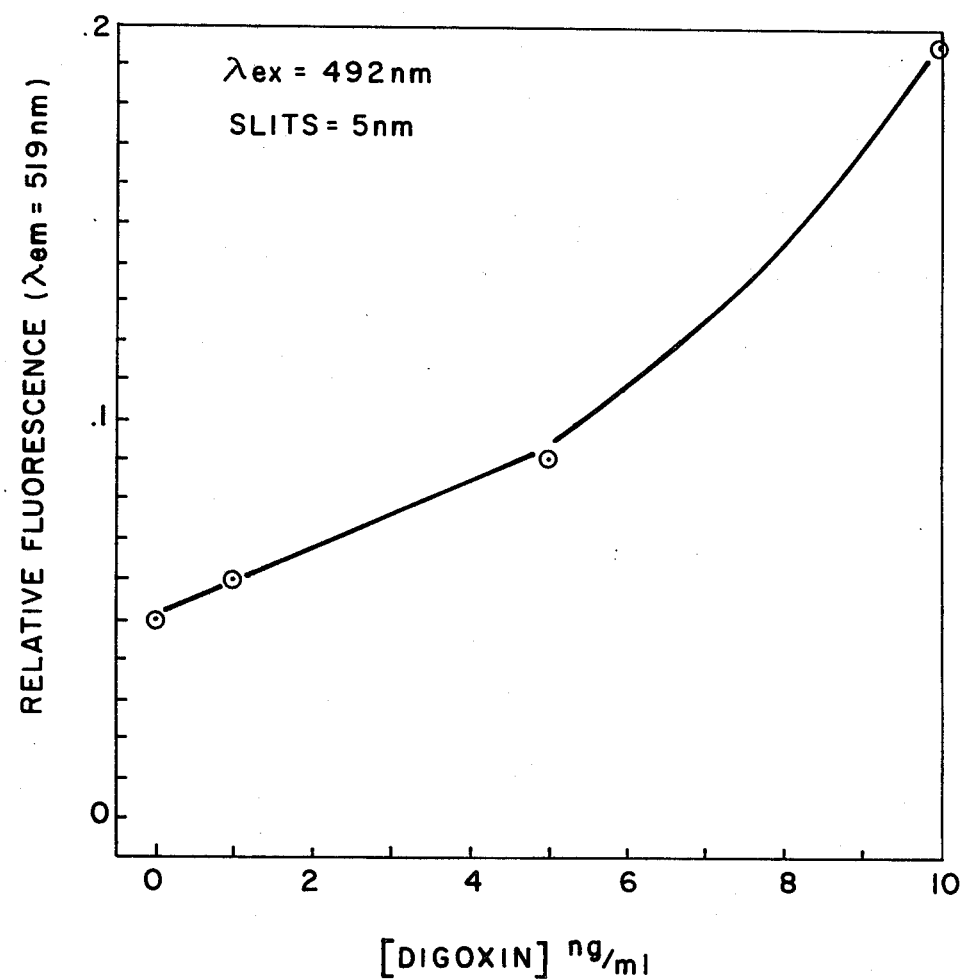
FIG. 1 shows the results of a digoxin assay performed according to the invention using a fluorescent anti-digoxin antibody.

For the purposes of this disclosure the following terms are defined as follows: analyte is an antigenic or haptenic substance, or group of substances, whose presence or the amount thereof in a liquid medium is to be determined; analyte-analogue is any substance, or group of substances, whose affinity for anti-analyte antibody is less than that of the analyte; monovalent antibody is an antibody or antibody fragment having only one binding site for antigen and can include Fab and Fab' fragments and half-molecules (heavy chain-light chain dimers) as described in co-pending application Ser. No. 374,971 filed May 5, 1982 incorporated herein by reference.

The labeling substance can be an enzyme, chromophore, fluorophore, chemiluminescent material, radioisotope, coenzyme, pigment particle, latex particle, or any other substance which is capable of generating a signal either by itself or in combination with other reagents.

In general, the labeling substance is chosen so as not to require overly complicated instrumentation for its detection and so as to be relatively immune to interference from normal constituents of body fluids. For these reasons, enzymes are generally preferred. Among those enzymes which have been widely used as labeling substances are β-galactosidase, horseradish peroxidase, and alkaline phosphatase. β-Galactosidase is generally preferred because it is not usually found in serum, has numerous chromogenic and fluorogenic substrates, and has a relatively high turnover number.

Analytes of interest can include proteins, peptides, hormones, drugs, vitamins, cell and tissue antigens, bacteria, viruses, etc. These are usually found in biological fluids such as whole blood, blood serum, blood plasma, urine, saliva, and cerebrospinal fluid, but can also be found on cells and in tissues.

Monovalent antibodies are produced by known methods. For example, Fab fragments are obtained by papain digestion of IgG [Porter, Biochem. J., Volume 73, 119 (1959)]; Fab' fragments are obtained by disulfide reduction of F(ab')$_2$ fragments obtained by pepsin digestion of IgG [Nisonoff, Methods Med. Res., Volume 10, 132 (1964)]; half-molecules are formed by sulfitolysis cf IgG as described in co-pending application Ser. No. 374,971, filed May 5, 1982, incorporated herein by reference. Intact IgG is sulfitolyzed with sodium sulfite (100 mM per mg IgG) in the presence of 5,5'-dithiobis(2-nitrobenzoic acid) (2.5 mM per mg IgG), preferably in a buffered medium at room temperature under nitrogen, to yield S-sulfonated half molecules of IgG. In general, it is desirable to immunopurify the antibody prior to its use in an immunoassay. Again, the methods for isolation of IgG from animal serum and the methods for its immunopurification by affinity chromatography are known. [Jaton, et al., Immunological Methods, Lefkovits & Perris, eds., New York: Academic Press, 1979, 44].

Although divalent antibodies can be used in the assay of this invention, sensitivity is improved by the use of monovalent antibodies, and the latter are, therefore, preferred. This is due to the fact that monosaturated divalent antibodies cannot be distinguished from unsaturated antibodies in terms of their binding behavior. If monovalent antibodies are employed, there will be a one-to-one correspondence between binding of sample analyte and displacement of labeled antibody from the solid phase.

Methods for coupling the labeling substance to the antibody are known. See, for example, Methods in Enzymology, van Vunakis & Langone (eds.), Volume 70 (1980), and references contained therein. In general, one should couple at least one label to each antibody, preferably covalently, and in such a manner as to preserve the immunoreactivity of the antibody. The free sulfhydryl groups present on Fab' fragments and the sulfonate group present on half-molecules provide specific reactive groups for covalent attachment of the label. Labeling of the antibody using these groups is known not to affect the immunoreactivity of the antibody. Heterobifunctional crosslinking reagents having maleimido or thiopyridyl groups are useful for the labeling [O'Sullivan et al., Methods in Enzymology, Volume 73, 147 (1981)]. Generally, it is desirable that the final step in the synthesis of the labeled antibody be an immunopurification step.

Analyte or analyte-analogue can be immobilized on a suitable solid phase by known methods. [Kiefer, Immunological Methods, Lefkovits & Perris, eds., New York: Academic Press, 1979, 137]. In the preferred mode, the solid phase is an affinity column packing material which is chosen for its flow characteristics and can include, for example, beaded agarose, polyacrylamide, glass, cellulose and cross-linked dextran. The analyte-analogue can be coupled covalently to the solid phase, either directly or through a spacer arm. The spacer arm can be, for example, a protein or polyamino acid.

Although the column packing material of an affinity column serves as the solid phase in the preferred embodiment of this invention, other solid phases are contemplated. For example, the solid phase can be the wall of a plastic test tube or microtiter plate. In these cases, the analyte-analogue can be immobilized by physical means, and the complexed displaced, labeled, anti-analyte antibody will be separated from the solid phase by decanting the reaction mixture.

The analyte-analogue should be chosen so as to have a substantially lower affinity for anti-analyte antibody than does the analyte itself. It is believed that the dissociation constant, $K_d$, of the antibody-(analyte-analogue) complex should be at least ten to one hundred times that of the antibody-analyte complex. In the embodiment in which an affinity column is used to effect the separation step, it is believed that the rate at which antibody dissociates from analyte-analogue must be fast compared to the rate at which sample elutes from the column. For example, in an embodiment of this invention used to detect digoxin, ouabain is chosen as the analyte-analogue because, while it can still bind to anti-digoxin antibody, the dissociation constant of the resulting complex is sufficiently greater than that of a digoxin complex so as to permit the assay to be performed rapidly and without the need for inclusion of a chaotropic agent. Other examples of useful analyte/analyte-analogue pairs include procainamide/N-acetyl-procainamide and theophylline/caffeine. It is expected that one should also be able to utilize partially denatured or chemically modified antigen as analogue; see, for example, Landsteiner, The Specificity of Serological Reactions, Cambridge: Harvard Press, (1945).

In the preferred embodiment, an affinity column is pre-saturated with an amount of labeled monovalent antibody known to be in molar excess over analyte. In this way, one is assured that every molecule of analyte will be able to displace one molecule of labeled antibody.

Because the labeled antibody can be present in excess, there is no need for very precise loading of the column, thus simplifying its synthesis. Slight variations in the amount of antibody on the column will not affect the accuracy or reproducibility of the measurements made.

Alternatively, one can perform the present invention in a batch mode rather than a column mode. In the batch mode, a slurry of affinity column packing material having analyte-analogue immobilized thereon and labeled, anti-analyte antibody bound thereto is added to a reaction vessel containing liquid sample. After a suitable incubation period, the vessel will be centrifuged and the supernatant fluid containing displaced antibody will be aspirated and analyzed.

In the preferred mode, the assay of this invention is performed as follows: A known volume of liquid sample, usually 5 μL to 500 μL, containing an unknown quantity of analyte is percolated through a column, preferably of dimensions 2 mm×10 mm, containing analyte-analogue immobilized on a column packing material and pre-saturated with an excess of labeled, monovalent anti-analyte antibody. The sample is eluted from the column at a flow rate of 0.2–5.0 mL per minute with a suitable buffer such as phosphate buffered saline, usually 1–5 mL total volume. The fraction which elutes from the column contains labeled antibody complexed with analyte from liquid sample. The activity of the label in this fraction is then measured and correlated by means of a standard curve to the concentration of analyte in the sample.

The assay of this invention can be performed manually or can be adapted to a variety of semi-automated or automated instrumentation, such as the aca ™ discrete clinical analyzer available from E. I. du Pont de Nemours and Company, Wilmington, Del. The following examples illustrate the invention.

EXAMPLE I

Fluorescent Immunoassay for Digoxin

Fluoresceinated α-digoxin antibodies were purchased from Cappel Laboratories as immunoglobulin (IgG) fraction. Divalent digoxin monospecific antibodies were purified from this fraction by affinity chromatography on a ouabain-affinity resin.

(A) Synthesis of Affinity Column Packing Material Having Oubain Immobilized Thereon Ouabain was attached to an agarose matrix through human serum albumin, HSA, as follows:

(1) A ouabain-HSA conjugate was synthesized. Ouabain (0.56 mmole dissolved in 20 mL of water) was oxidized with sodium metaperiodate (1.02 mmole) for 1 hour at room temperature in the dark. Quantitative oxidation was verified by thin layer chromatography on silica gel G plates developed in ethyl acetate:methanol:H$_2$O (75:25:1 by volume). The excess periodate was removed by passing the aqueous mixture through a 3 mL column of DOWEX AG-1X8 which is a strong basic anion exchange resin with quaternary ammonium exchange groups attached to a styrene-divinylbenzene copolymer lattice. Quantitative recovery of ouabain was verified by following radiolabeled (tritiated) ouabain. The solution of oxidized ouabain was buffered to pH 9.5 with the addition of 0.4 mL of 5% Na$_2$CO$_3$ and combined with 20 mL of HSA solution (28 mg/mL). After 45 minutes, the conjugate was reduced with the addition of 0.3 gm of sodium borohydride freshly dissolved in 20 mL of water. Three hours later, 8 mL of 1 M formic acid was added to lower the pH to 6.5. After 1 hour at pH 6.5, the pH was raised to pH 7.5 with 1 M NH$_4$OH. The entire reaction mixture was dialyzed extensively against distilled water, and then finally against 0.015 M sodium phosphate buffer, pH 7.8, 0.15 M NaCl. The conjugate was concentrated on an Amicon PM-30 membrane (inert, nonionic, polymeric membrane with macrosolute retention cut-off of 30,000 daltons) to 4.2 mg/mL. Protein concentration was determined by the method of Lowry. [Lowry, O H., et al.(1951) J. Biol. Chem., 193, 265.]

(2) The ouabain-HSA conjugate was immobilized on material sold under the trade name Affi-Gel ®10 (Bio-Rad Laboratories). This material is a 6% beaded agarose matrix having a long hydrophilic chemical spacer arm terminating in a N-hydroxy succinimidyl ester for chemical attachment of ligands such as proteins via their amino groups. The immobilization procedure was as follows: 25 mL of Affi-Gel ®was washed with 75 mL of ice-cold water. The gel was added to the concentrated ouabain-HSA conjugate and allowed to mix on a rocker overnight at 4° C. The excess active ester groups were blocked by adding 0.1 mL of 1 M ethanolamine, pH 8.0, for 1 hour at room temperature. Finally, the gel was washed extensively with distilled water, and then in turn with 500 mL of 0.5 M NaCl; 400 mL of 0.1 M glycine, pH 2.5; 300 mL of 2.5 M NH$_4$SCN; 1000 mL of phosphate buffered saline. The column packing material (also referred to as "resin") was stored at 4° C. in the presence of 0.02% sodium azide.

(B) Affinity Purification of Anti-Digoxin

Digoxin-specific antibodies were immunopurified directly from an IgG fraction using the following representative protocol: The column packing material as prepared in A(2) above was packed into a column (0.7 cm×15 cm) to a bed volume of 6 mL and equilibrated with phosphate buffered saline. As used in this disclosure, all column dimensions are expressed as diameter in centimeters×height in centimeters. Antiserum (10 mL of Cappel α-digoxin serum at 4.5 mg/mL monospecific antibody) was applied at a flow rate of 1 mL per minute. The column was washed with phosphate buffered saline until the absorbance at 280 nm reached baseline. Antibody was then eluted from the column with 60 mL of 3 M NH4SCN (pH 7.5) and immediately dialyzed against 4×2 L changes of phosphate buffered saline at 4° C.

(C) Digoxin Assay

Measurement of sample digoxin was performed in the following manner: a ouabain-affinity column as prepared in (B) above (0.5 cm×8 cm) was loaded with a solution of fluoresceinated affinity-purified antibodies (10 mL at 0.4 mg/mL) and then washed with 50 mL of phosphate buffered saline containing 1 mg/mL HSA. Samples (500 μL) containing various amounts of digoxin in a solution of phosphate buffered saline containing HSA were percolated through the column followed by 4.5 mL of the same albumin-buffer solution at a flow rate of 0.5 mL per minute. The fluorescence in the eluates was then measured in an Aminco Spectrofluorometer and plotted as a function of the digoxin concentration in the original sample. The results are shown in FIG. 1.

EXAMPLE II

Enzyme Immunoassay for Digoxin

The antibody reagent used in this example was a conjugate prepared by binding the monovalent antibody fragment Fab' to β-galactosidase using the heterobifunctional reagent m-maleimidobenzoyl-N-hydroxysuccinimide ester (MBS).

(A) PREPARATION OF Fab' β-GALACTOSIDASE CONJUGATE

Digoxin-specific antibodies were immunopurified directly from whole rabbit serum using the following representative protocol: Ouabain affinity resin was packed into a column (0.7 cm×15 cm) to a bed volume of 6 mL and equilibrated with phosphate buffered saline. Antiserum (10 mL of Cappel α-digoxin serum at 4.5 mg/mL monospecific antibody) was applied at a flow rate of <1 mL per minute. The column was washed with phosphate buffered saline until the absorbance at 280 nm reached baseline (<0.01). Antibody was then eluted from the column with 60 mL of 3 M NH4SCN (pH 7.5) and immediately dialyzed against 4×2 L changes of phosphate buffered saline at 4° C.

Fab' fragments were prepared from affinity purified antibodies via pepsin digestion. Twenty mL of affinity-purified α-digoxin antibodies was concentrated to 2 mL on an Amicon stirred-cell apparatus (PM-30 membrane). The final protein concentration was measured to be 10 mg/mL. The sample was dialyzed against 1000 mL of 0.1 M sodium acetate, pH 4.5, for 4 hours at 4° C. After dialysis, 20 μL of a 10 mg/mL solution of pepsin, dissolved in the same sodium acetate buffer, was added and the temperature raised to 37° C. for 20 hours. After this digestion period, the sample was clarified by a brief centrifugation and then chromatographed on a Sephadex G-150 (cross-linked, beaded dextran having 150,000 dalton exclusion limit) column (1.5 cm×90 cm) equilibrated in 0.015 M sodium phosphate (pH 7.4), 0.15 M NaCl (phosphate buffered saline). The column fractions containing the (Fab')2 fragments, identified by gel electrophoresis, were pooled (19.2 mL) and then concentrated to 2.0 mL by pressure filtration (PM-30 Amicon membrane). After concentration, the (Fab')2 fragments were reduced to their corresponding Fab' fragments by adding 40 μL of a 1 M dithiothreitol solution. The reduction was performed at 25° C. for 90 min under argon. The Fab' fragments were then reacted with 14.8 mg of iodoacetamide at 25° C. for 2 hours under argon. Reaction products were removed by dialysis at 4° C. against 3×4 liters of phosphate buffered saline.

The Fab' fragments so produced were then reacted with a 20-fold molar excess of MBS. Eighty-five microliters of a 79 mM solution of MBS in tetrahydrofuran was added to the 2 mL solution of Fab' fragments and reacted for 1 hr. at 25° C. under argon. The mixture was desalted on a Sephadex G-25 (cross-linked, beaded dextran having 5000 dalton exclusion limit) column (1.5 cm×40 cm) in phosphate buffered saline. The derivatized Fab' fragments, which eluted in the void volume, were pooled and combined with 2 mL of β-galactosidase at 12 mg/ml in phosphate buffered saline at 4° C. After 16 hours, this solution was concentrated to 2 mL on an Amicon PM-30 pressure filtration stirred-cell followed by column chromatography on Sepharose 4B-CL (cross-linked, macroporous agarose in bead form having $1-5\times10^6$ dalton exclusion limit in a 1.5 cm×90 cm column). The Fab'-β-galactosidase conjugate was eluted with the free β-galactosidase. The entire peak of enzyme activity was pooled and subsequently immunopurified on the ouabain affinity column. The procedure for immunopurification was as follows: Pooled column fractions from the Sepharose 4B-CL column were eluted through the ouabain affinity column (1.0 cm×7.0 cm), followed by 100 mL of phosphate buffered saline. The Fab'-β-galactosidase conjugate was then eluted with 50 mL of 23 mM ouabain in phosphate buffered saline. This eluate represented the final reagent and was dialyzed against 6×4 L of phosphate buffered saline at 4° C.

(B) Digoxin Assay

Figure 2:
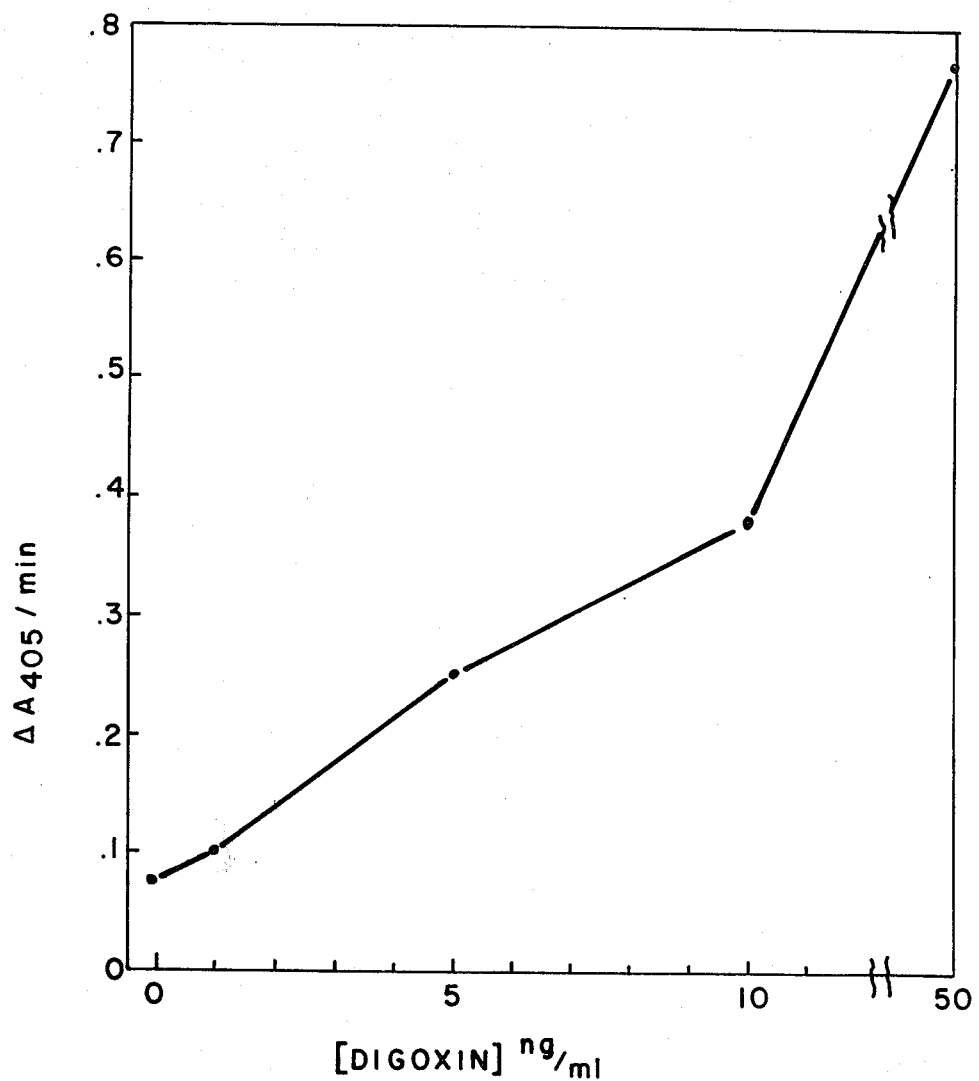
FIG. 2 shows the results of a digoxin assay performed according to the invention using an enzyme-labeled anti-digoxin antibody.

Measurement of digoxin in the test sample was performed in the following manner: A ouabain-affinity column as described in Example I (0.5 cm×4 cm) was loaded with a solution of Fab'-β-galactosidase conjugate and then washed with 50 mL of phosphate buffered saline. Samples (200 μL) of human serum containing various amounts of digoxin were eluted through the column followed by 1 mL of phosphate buffered saline. The flow rate was approximately 0.5 mL per minute. The β-galactosidase activity in the eluates was determined spectrophotometrically upon the addition of the substrate o-nitrophenylgalactoside to a final concentration of 7.5 mM at 37° C. The enzyme activity ($A_{405}$ per min.) is plotted in FIG. 2 as a function of digoxin concentration in the 200 μL samples.

I claim:

1. A method for determining the amount of an analyte in a liquid sample, comprising the following steps:
   (1) contacting a liquid sample suspected of containing analyte with a solid phase having immobilized thereon an analyte-analogue to which there is displaceably bound a labeled, anti-analyte antibody in molar excess over the analyte, wherein the dissociation constant between said antibody and the analyte-analogue is greater than the dissociation constant between said antibody and the analyte, whereby said antibody is displaced from the immobilized analyte-analogue as said antibody forms a complex with the analyte from the liquid sample;

(2) separating said complex from the solid phase; and
(3) measuring the amount of said complex which is related to the amount of analyte initially present in the liquid sample.

2. The method of claim 1 wherein the labeled anti-analyte antibody is a monovalent antibody selected from the group consisting of Fab, Fab' and half-molecules.

3. The method of claim 1 wherein the label is an enzyme, chromophore, fluorophore, chemiluminescent material, radioisotope or coenzyme.

4. The method of claim 1 wherein the analyte is a protein, peptide, hormone, drug, vitamin, cell antigen, tissue antigen, bacterium or virion.

5. The method of claim 1 wherein the solid phase is an affinity column packing material or a plastic surface.

6. The method of claim 5 wherein the affinity column packing material is beaded agarose, polyacrylamide, glass, cellulose or cross-linked dextran.

7. The method of claim 1 wherein the separation step comprises percolating the liquid sample through a column containing an affinity column packing material.

8. The method of claim 7 wherein the analyte is digoxin, the analyte-analogue is oubain, the antibody is labeled anti-digoxin antibody and the solid phase is a beaded agarose matrix.

9. The method of claim 8 wherein the label is fluorescein or $\beta$-galactosidase.

10. The method of claim 9 wherein the labeled anti-digoxin antibody is a $\beta$-galactosidase-labeled anti-digoxin-Fab' fragment and the amount of complex is measured by reacting said complex with o-nitrophenyl-galactoside.

* * * * *